United States Patent [19]

Vlachakis

[11] 4,311,790

[45] Jan. 19, 1982

[54] RADIOENZYMATIC METHOD FOR ASSAYING 3,4-DIHYDROXYPHENYLGLYCOL

[75] Inventor: Nicholas D. Vlachakis, Altadena, Calif.

[73] Assignee: The University of Southern California, Los Angeles, Calif.

[21] Appl. No.: 55,582

[22] Filed: Jul. 9, 1979

[51] Int. Cl.$^3$ .................. G01N 33/48; C12N 9/10
[52] U.S. Cl. .................. 435/15; 23/230 B; 424/1; 435/193
[58] Field of Search .......... 23/230 B; 424/1, 1.5, 424/12; 435/7, 4, 15, 193, 810

[56] References Cited

U.S. PATENT DOCUMENTS 4,242,456  12/1980  Johnson et al. .................. 435/193

OTHER PUBLICATIONS

Peuler et al., Life Sciences, vol. 21, 1977, pp. 625–636.
Saller et al., Life Sciences, vol. 23, 1978, pp. 1117–1130.
Martin et al., Chem. Abstracts, vol. 90, Apr. 9, 1979, Abstract No. 117415p.
Eriksson et al., Chem. Abstracts, vol. 88, Mar. 13, 1978, Abstract No. 71119y.

*Primary Examiner*—Benjamin R. Padgett
*Assistant Examiner*—Christine M. Nucker
*Attorney, Agent, or Firm*—Nilsson, Robbins, Dalgarn, Berliner, Carson & Wurst

[57] ABSTRACT

A method for assaying 3,4-dihydroxyphenylglycol in a sample containing other catechol compounds by forming tritiated O-methylated derivatives, extracting tritiated 3-methoxy-4-hydroxyphenylglycol at a pH of 5 or lower, isolating the tritiated 3-methoxy-4-hydroxyphenylglycol and measuring its radioactivity. Prior to measurement, the tritiated 3-methoxy-4-hydroxyphenylglycol can be oxidized to tritiated vanillin which is extracted into the counting solution to increase specificity of the assay.

11 Claims, No Drawings

RADIOENZYMATIC METHOD FOR ASSAYING 3,4-DIHYDROXYPHENYLGLYCOL

FIELD OF THE INVENTION

The field of art to which the invention pertains includes the field of catechol assay and radioenzymatic analysis.

BACKGROUND AND SUMMARY OF THE INVENTION

Knowledge of the fate of released catecholamines from nerve terminals may help to elucidate the role of the sympathetic system in the pathogenesis of hypertension and other diseases in which abnormal sympathetic function has been implicated. For example, experiments carried out with radioactive catecholamines or their precursors have indicated that the deaminated glycol 3,4-dihydroxyphenylglycol (DOPEG), is formed intraneuronally from norepinephrine leaking from granules into the neuronal cytoplasm or from neuronal reuptake of released norepinephrine, and extraneuronally, together with the deaminated acid 3,4-dihydroxymandelic acid by the action of enzyme monoamine oxidase. Accordingly, it is desirable to be able to quantitatively assay DOPEG to the exclusion of other cathecholamine and catecholamine metabolites.

Various techniques for the measurement of urinary catecholamines and catecholamine metabolites have been developed and applied in many laboratories but most of these methods are non-specific and laborious. The advent of analyses based on radioenzymatic assay techniques make possible the accurate measurement of plasma and tissue catecholamines in small quantities of specimens. See for example the paper by Peuler and Johnson: "Simultaneous Single Isotope Radioenzymatic Assay of Plasma Norepinephrine, Epinephrine and Dopamine," Life Sciences Vol. 21, pp. 625–636 (1977) which describes an assay in which catecholamines are converted to their tritiated O-methylated derivates. Conversion occurs in an incubation mixture by transmethylation with S-adenosyl-L-methionine having a tritiated methyl group, promoted by the transfer enzyme catechol-O-methyl transferase. The tritiated catecholamines are extracted into an organic solvent and separated by thin layer chromatography. Increased specificity is obtained, excluding O-methylated compounds that lack a beta-hydroxyl group by oxidation of at least a portion of the zone scrapings to tritiated vanillin. Measurement of the radioactivity of the tritiated vanillin then constitutes a means for quantitative determination of the chromatographically separated catecholamines.

While the Peuler and Johnson method is useful for measuring catecholamines, the form of assay presented by Peuler and Johnson has not been found useful for the determination of metabolically deaminated products such as 3, 4-dihydroxyphenylglycol. The present disclosure provides a means for assaying 3,4dihydroxyphenylglycol and can be described as a modification of the Peuler and Johnson method. In particular, I have found that by extracting product from the incubation mixture at a pH of 5 or lower, one can decrease the extractability of the catecholamines but increase the extractability of 3-methoxy-4-hydroxyphenylglycol which is the O-methylated derivative of DOPEG. The result is a rapid, specific and inexpensive assaying method for the quantitative measurement of 3, 4-dihydroxyphenylgylcol. The method yields results in less than three hours while one person could easily perform 24 assays in eight hours.

More particularly, a method is provided for assaying 3,4-dihydroxyphenylglycol in a sample containing other catechol compounds, in which an incubation mixture is formed having a pH greater than 7 containing the sample and containing S-adenosyl-L-methionine having a tritiated methyl group and catechol-O-methyl transferase. The mixture is incubated for a time sufficient to transmethylate the 3,4-dihydroxyphenylglycol with the tritiated methyl group to form tritiated 3-methoxy-4-hydroxyphenylglycol. The pH of the incubation mixture is then lowered to 5 or lower and the tritiated 3-methoxy-4-hydroxyphenylglycol is extracted from the lower pH mixture into an organic solvent such as a mixture of toluene and isoamyl alcohol. The tritiated 3-methoxy-4-hydroxyphenylglycol is separated from the organic solvent and isolated, preferably by thin layer chromatography. Also in a preferred step, the separated tritiated 3-methoxy-4-hydroxyphenylglycol is oxidized to tritiated vanillin and combined with a counting solution. By decreasing the pH in the counting solution to about 4.5, extraction is optimal for vanillin which can then be radioactively measured as a quantitative measure of the 3, 4-dihydroxyphenylglycol.

The pH of the incubation mixture can be lowered by the addition of an acid such as glacial acetic acid to achieve for example a pH of 1.5, so that when the incubation mixture is combined with organic solvent having a pH of about 7, the extraction takes place at a pH of 5 or lower. Conducting the extraction at a pH of 5 or lower is critical to success of this assay method as it results in a decrease in extraction of both normetanephrine and metanephrine and a marked increase in the extractability of 3-methoxy-4-hydroxyphenylglycol.

DETAILED DESCRIPTION

In assaying for 3, 4-dihydroxyphenylglycol, the sample to be analyzed can be placed in a tube along with preservatives and stored at reduced temperature until analysis. O-methylation is accomplished by transmethylation using commercially available tritiated S-adenosyl-L-methionine, having one or more hydrogen atoms on its methyl group substituted with tritium $^3H$), promoted by the transfer enzyme catechol-O-methyl transferase. Preferably the sample is buffered, e.g., to a pH in the range of 8.0–8.8 to facilitate the transmethylation. An internal standard consisting of a known amount of 3, 4-dihydroxyphenylglycol can be added to a duplicate sample for concurrent processing and a blank can be prepared for concurrent processing made up of the reagents alone without the sample and without the standard. The reaction mixture is incubated for a time sufficient to assure the completion of reaction.

While in the Peuler and Johnson method, incubation is terminated by raising the pH to 10.0, in accordance with the present invention, it is terminated by lowering the pH preferably by the addition of an acid such as glacial acetic acid. The resultant mixture has a pH of approximately 1.5 which is then mixed with an appropriate amount of organic solvent having a pH of approximately 7 to result in extraction at a pH of 5 or lower.

The O-methylated products are then partitioned into an aqueous acetic acid layer and subjected to thin layer chromatography using known techniques, such as by using an automatic thin layer chromatography Multispotter, spotting the mixture on silica gel plates. The plates can be developed in a known but specific developing solution which permits separation of 3-methoxy-4-hydroxyphenylglycol from other O-methylated compounds, whereas many other solutions do not allow that. The plates are then dried and bands corresponding to the separated catechols can be located by inspection, for example under short wave ultraviolet light. The target band of tritiated 3-methoxy-4-hydroxyphenylglycol can be scraped into a scintillation vial. To further increase the specificity of the assay, the tritiated derivative is then oxidized to vanillin by the addition of sodium metaperiodate in ammonium hydroxide, followed by reduction of the pH to about 4.5 to extract the tritiated vanillin into the organic phase of added scintillation fluid. The vials can then be placed into a liquid scintillation counter and the counts per minute of the organic phase determined. The amount of 3, 4-dihydroxyphenylglycol as tritiated vanillin can be determined using the following formula:

$$\frac{CPM_{sample} - CPM_{blank}}{CPM_{(standard+sample)} - CPM_{sample}} \times 500 \times 20 = pg/ml \text{ of sample}$$

Accordingly, one can determine the count per minute (CPM) of the sample, the blank, and the sample plus internal standard, and applying the above formula, one can obtain in picograms the amount of 3, 4-dihydroxyphenylglycol per milliliter of sample.

The following examples serve to further illustrate the invention.

EXAMPLE 1

Preparation of Catechol-O-Methyl Transferase (COMT)

A modification of the method Axelrod and Tomchick was used for preparation of COMT, as reported in *Enzymatic O-Methylation of Epinephrine and Other Catechols*, J. Biol. Chem., 233, 702 (1958). 10 male Sprague-Dowley rats were killed by decapitation and their livers were removed quickly and chilled. 100 Grams of liver were homogenized in 400 milliliters of isotonic potassium chloride and centrifuged at 78,000 g for 30 minutes in a cold ultracentrifuge. The supernatant was decanted, pH was adjusted to 5 with 1 molar acetic acid, allowed to stand for 20 minutes and recentrifuged at 30,000 g for 15 minutes. To 300 milliliters supernatant, 52 grams of ammonium sulphate was slowly added, the mixture was allowed to stand for 10 minutes and then centrifuged at 30,000 g for 15 minutes. To the supernatant, 34 grams of ammonium sulphate was added and allowed to stand for 10 minutes. The resultant precipitate was washed with 55% ammonium sulphate and then dissolved in 35 milliliters of 1 millimolar phosphate buffer of pH 7.4, which was dialyzed over 18 hours against the phosphate buffer containing 0.1 millimolar dithiothreitol. The dialyzed enzyme was centrifuged at 16,000 g for 10 minutes, divided into 0.5 milliliter aliquots and stored at −30° C. in plastic tubes. Protein concentration was 20 mg/ml. Activity was found to be retained for at least 12 months.

Sample Preparation

Blood was collected into tubes containing reduced glutathione, as antioxidant, and ethylenebis (oxyethylene-nitrilo) tetraacetic acid (EGTA), as chelating agent. 20 microliters of a stock solution containing 1.2 grams glutathione and 2.6 grams EGTA in 20 milliliters of water, pH 5.5, was added to each milliliter of blood, which then was centrifuged at 1600 g for 10 minutes at 4° C. and the plasma stored at −20° C. until analysis. Before analysis the sample was thawed and centrifuged again.

Assay Procedure

50 Microliters of the plasma were transferred to a 13×100 mm disposable borosilicate tube containing 5 microliters (2.5 μCi) of tritiated S-adenosyl-L-methionine ($^3$H-SAME) (a commercially available material obtained from New England Nuclear Corporation having a specific activity of 10.3 Ci/mMole) and 10 microliters of a buffer from a stock solution containing 1 Mole of Tris-HCl, 0.5 Mole of MgCl$_2$ and 0.1 Mole of EGTA in 100 milliliters of water, pH 8.0. The magnesium ion appears to be a necessary cofactor for the transfer enzyme. An internal standard, consisting of 500 picograms, of 3, 4-dihydroxyphenylglycol in 10 microliters of water, was added to another tube containing the sample. A blank was prepared by adding 50 microliters of deionized water to a third tube containing buffer and isotope.

Reaction was initiated by the addition of 10 microliters of COMT. The reaction mixture was incubated for 60 minutes at 37° C. in a shaking water bath. The incubation was then terminated by the addition of 150 microliters of glacial acetic acid. 20 Microliters of non-radioactive carrier solution containing 25 micrograms each of normetanephrine, metanephrine, vanillyl mandelic acid and 3-methoxy-4-hydroxyphenylglycol, were added to each tube to aid in visualization and better delineation of the thin layer chromatography spots. The O-methylated products were extracted with 3 milliliters of toluene:isoamyl alcohol (3:2, v/v) by mixing on a vortex for 30 seconds. The tubes were centrifuged at 800 g for 2 minutes and the organic phase was transferred (after quick freeze in a dry ice-acetone bath) into centrifuge tubes, each containing 150 microliters of 0.1N acetic acid. The tubes were vortexed for 30 seconds, centrifuged at 800 g for 2 minutes and the supernatant organic phase was aspirated off. The acetic acid was transferred to 250 microliter syringes.

By using the automatic thin layer chromatography Multispotter, the acetic acid was spotted on silica gel plates. The plates were developed for one hour in a tank containing a mixture of chloroform:alcohol:40% in water methylamine (80:15:10) and air dried. Bands corresponding to metanephrine, normetanephrine, 3-methoxy-4-hydroxyphenylglycol and vanillylmandelic acid were located by inspection under short-wave ultraviolet light. The 3-methoxy-4-hydroxyphenylglycol bands were scraped into scintillation vials to which were added 1 milliliter of 1M NH$_4$OH. After gently shaking for a few seconds the tritiated derivatives were oxidized to vanillin by the addition of 100 microliters of 4% NaIO$_4$, allowed to stand for 5 minutes and the pH was brought down to 4.5 by adding 100 microliters of glacial acetic acid. 10 milliliters of toluene/Liquiflor (obtained from New England Nuclear Company) was added followed by one milliliter of 0.1N acetic acid. The vials were covered tightly and vigorously shaken for a few seconds to extract the vanillin into the organic phase. The organic phase was counted in a liquid scintillation counter at 8° C. The endogenous amount of 3, 4-dihydroxyphenylglycol in 50 microliters of sample was calculated as follows:

$$\frac{CPM_{sample} - CPM_{blank}}{CPM_{(standard+sample)} - CPM_{sample}} \times 500 \times 20 =$$

pg/ml of sample

Results

The following table lists 3, 4-dihydroxyphenylglycol assayed in the plasma of 16 subjects comprised of 6 normotensive and 10 hypertensive subjects at rest and during sympathetic stimulation induced by head-up tilt and isometric handgrip contraction. The results are expressed as mean ± the Standard Error of the Mean.

TABLE I

| Phase of Study | 3,4-dihydroxyphenylglycol pg/ml of plasma |
|---|---|
| Recumbent - 30 min. | 792 ± 63 |
| Head-up tilt - 5 min. | 787 ± 70 |
| Head-up tilt 15 min. | 879 ± 77 |
| Head-up tilt 30 min. | 907 ± 73 |
| Post-tilt recumb. - 5 min. | 876 ± 51 |
| Post-tilt recumb. 15 min. | 800 ± 54 |
| plus 3 min. THC* | 823 ± 55 |

*THC = isometric handgrip contraction for 3 minutes in the recumbant position at 50% of the maximal contraction capacity.

Specificity

The enzyme COMT is specific for catechols. However, the specificity of the assay increases by the fact that the different O-methylated catecholamine derivatives have different extractability into toluene: isoamyl alcohol and different $R_f$ values during the chromatographic step. At pH 10 there is optimal extractability for normetanephrine and metanephrine, but the extraction of 3-methoxy-4-hydroxyphenylglycol is minimal and no vanillylmandelic acid is extracted. Decreasing the pH toward 7 causes a progressive decrease in extraction of both metanephrines, and an increase in 3-methoxy-4-hydroxyphenylglycol and vanillylmandelic acid, but there is a substantial increase in the blank values of all compounds. By decreasing the pH to 5 or lower, for example pH 4, extraction of the metanephrines was decreased approximately 35% as compared to extraction at pH 10, but the extractability for both 3-methoxy-4-hydroxyphenylglycol and vanillylmandelic acid increased substantially, whereas all blanks were relatively low. In 60 minutes with the solvent system employed in the assay, metanephrine and normetanephrine exhibited $R_f$ values of 0.35 and 0.27, respectively, where the $R_f$ value for 3-methoxy-4-hydroxyphenylglycol and vanillylmandelic acid were 0.22 and 0, respectively. A further increase of the specificity of the assay was obtained by oxidation of the O-methylated derivatives to vanillin because some O-methylated compounds, by lacking a beta-hydroxyl group in their structure, are not converted to vanillin. By decreasing the pH of the counting solution to 4.5 extraction was optimal for vanillin, whereas blanks were markedly reduced because nonspecific radioactivity was eliminated from the organic layer of the counting solution.

EXAMPLE 2

To demonstrate substrate specificity, assays were conducted as in Example 1 but in which there were added to individual tubes 1 nanogram of each of the substrates listed in Table II. Thus, one tube was a blank whereas another tube contained 50 microliters of plasma. In other tubes, in addition to the 50 microliters of plasma there were added 1 nanogram respectively of norepinephrine (NE), epinephrine (E), octopamine, 3-methoxy-4-hydroxyphenylglycol (MOPEG), 3,4-dihydroxyphenylglycol (DOPEG), 3,4-dihydroxymandelic acid (DOMA) or vanillylmandelic acid (VMA). The results shown in Table II were found expressed as CPM per nanogram of substrate together with 50 microliters of human plasma. Each value is the average of a duplicate assay.

TABLE II

| Assay Substrate Specificity | |
|---|---|
| Substrate | CPM |
| blank | 52 |
| plasma, 50 1 | 530 |
| NE | 546 |
| E | 614 |
| octopamine | 475 |
| MOPEG | 501 |
| DOPEG | 13,304 |
| DOMA | 609 |
| VMA | 488 |

Referring to Table II, it can be seen that the addition of an equal amount of each of the various listed substrates other than DOPEG did not exert any substantial effect on the CPM found, whereas the DOPEG addition resulted in a marked increase in CPM.

EXAMPLE 3

The procedure of Example 1 can be followed, but in place of the plasma sample one can use cerebrospinal fluid or urine. The fluid can be stored at −20° C. after adding 20 microliters per milliliter of the glutathione-EGTA solution of Example 1. Before analysis, the sample is thawed and 50 microliters can be used as the sample.

EXAMPLE 4

The procedure of Example 1 can be followed but in place of the plasma sample one can use human tissues. The tissues are immediately frozen on dry ice following excision and stored at −80° C. They are prepared by homogenization in 30 volumes (W/V) of 0.1 N perchloric acid. The homogenate is left on ice for 15 minutes, centrifuged at 1600 g at 4° C. for 15 minutes and the supernatant stored at −20° C. until analysis. Before analysis, the sample is thawed and centrifuged again. 25 Microliters of the tissue supernatant is used in place of the 50 microliters of plasma used in Example 1.

In various experiments it was found that excellent linearity of product forms from 25 pg to at least 5 ng. The sensitivity of the assay, measured as the amount of the compound which yields twice the blank value, was found to be 5 g for 3, 4-dihydroxyphenylglycol; in comparison sensitivity was found to be 8 pg for norepinephrine, 3 pg for epinephrine and 60 pg for 3, 4-dihydroxymandelic acid.

I claim:

1. In a radioenzymatic method for assaying a catechol compound by conversion of the catechol compound to its tritiated O-methylated derivative, extraction with organic solvent and measurement of the radioactivity of extracted material, the improvement, applied to assaying 3, 4-dihydroxyphenylglycol, according to which said catechol compound is 3,4-dihydroxyphenylglycol and said extraction is conducted at a pH of about 1.5 to 5 to obtain tritiated 3-methoxy-4-hydroxyphenylglycol as an extract.

2. The improvement according to claim 1 in which said extracted tritiated 3-methoxy-4-hydroxyphenylglycol is isolated by thin layer chromatography prior to said measurement.

3. The improvement according to claim 2 in which said isolated tritiated 3-methoxy-4-hydroxyphenylglycol is oxidized to tritiated vanillin to constitute said tritiated vanillin as said extracted material.

4. The improvement according to any of claims 1–3 in which said conversion of 3,4-dihydroxyphenylglycol is conducted by mixture with a transmethylation agent having a tritiated methyl group and incubation of said mixture at a pH greater than 7, said incubation being terminated by adding to said incubation mixture a quantity of acid sufficient to lower the pH to about 1.5 to 5.

5. The improvement according to claim 4 in which said acid is acetic acid.

6. The improvement according to any of claims 1–3 in which said organic solvent is a mixture of toluene and isoamyl alcohol.

7. The improvement according to claim 5 in which said organic solvent is a mixture of toluene and isoamyl alcohol.

8. A method for assaying 3, 4-dihydroxyphenylglycol in a sample containing other catechol compounds, comprising:

forming an incubation mixture having a pH greater than 7 containing said sample and containing S-adenosyl-L-methionine having a tritiated methyl group and catechol-O-methyl-transferase;

incubating said mixture for a time sufficient to transmethylate said 3, 4-dihydroxyphenylglycol with said tritiated methyl group to form tritiated 3-methoxy-4-hydroxyphenylglycol;

lowering the pH of said incubated mixture to a pH of about 1.5 to 5 and extracting said tritiated 3-methoxy-4-hydroxyphenylglycol from said lower pH mixture into organic solvent;

separating said tritiated 3-methoxy-4-hydroxyphenylglycol from said organic solvent including the step of isolating said 3-methoxy-4-hydroxyphenylglycol by thin layer chromatography;

oxidizing said separated tritiated 3-methoxy-4-hydroxyphenylglycol to tritiated vanillin; and measuring the radioactivity of said tritiated vanillin.

9. The method of claim 8 in which said organic solvent is a mixture of toluene and isoamyl alcohol.

10. The method of claim 8 or 9 in which the lowering of the pH of said incubation mixture is accomplished by the addition thereto of acid.

11. The method of claim 10 in which said acid is glacial acetic acid.

* * * * *

UNITED STATES PATENT AND TRADEMARK OFFICE
CERTIFICATE OF CORRECTION

PATENT NO. : 4,311,790
DATED : January 19, 1982
INVENTOR(S) : Nicholas D. Vlachakis It is certified that error appears in the above-identified patent and that said Letters Patent are hereby corrected as shown below:

Column 1, line 59, delete "3,4dihydroxyphenyl-" and insert
 --3,4-dihydroxyphenyl- --.

Column 6, line 54, delete "5 g" and insert --5 pg--.

Signed and Sealed this

Twenty-ninth Day of June 1982

[SEAL]

Attest:

GERALD J. MOSSINGHOFF

*Attesting Officer*  *Commissioner of Patents and Trademarks*